(12) United States Patent
Ostuni et al.

(10) Patent No.: US 7,288,394 B2
(45) Date of Patent: Oct. 30, 2007

(54) SELECTIVE DEPOSITION OF MATERIALS ON COUNTOURED SURFACES

(75) Inventors: Emanuele Ostuni, Watertown, MA (US); Christopher S. Chen, Baltimore, MD (US); Donald E. Ingber, Boston, MA (US); George M. Whitesides, Newton, MA (US)

(73) Assignees: President & Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 305 days.

(21) Appl. No.: 10/668,679

(22) Filed: Sep. 23, 2003

(65) Prior Publication Data

US 2004/0171135 A1    Sep. 2, 2004

Related U.S. Application Data

(63) Continuation of application No. PCT/US02/09149, filed on Mar. 25, 2002.

(60) Provisional application No. 60/278,092, filed on Mar. 23, 2001.

(51) Int. Cl.
*C12N 11/02* (2006.01)
*C12N 11/08* (2006.01)
*C07K 17/02* (2006.01)
*C07K 17/08* (2006.01)

(52) U.S. Cl. ............ 435/177; 435/180; 530/812; 530/815

(58) Field of Classification Search ............ None
See application file for complete search history.

(56) References Cited

U.S. PATENT DOCUMENTS

| 5,512,131 A | 4/1996 | Kumar et al. |
| 5,900,160 A | 5/1999 | Whitesides et al. |
| 5,976,826 A | 11/1999 | Singhvi et al. |
| 6,001,587 A | 12/1999 | Turner et al. |
| 6,180,239 B1 | 1/2001 | Whitesides et al. |
| 6,518,168 B1 * | 2/2003 | Clem et al. ............ 438/623 |
| 6,893,850 B2 * | 5/2005 | Ostuni et al. ............ 435/174 |

FOREIGN PATENT DOCUMENTS

| WO | WO96/29629 A2 | 9/1996 |
| WO | WO99/54786 A1 | 10/1999 |
| WO | WO 01/70389 A2 | 9/2001 |
| WO | WO 02/086452 A2 | 10/2002 |

OTHER PUBLICATIONS

PCT/US02/09149, *International Search Report* dated Nov. 21, 2002.
You, A.J. et al., *Chem. & Biol.* 1997, 4, 969-975.
Parce, J.W. et al., *Science* 1989, 246:243-247.
Ostuni, E. et al., *Langmuir* 2000, 16;7811-7819.
Xia, Y. et al., *Agnew. Chem. Int. Ed. Engl.* 1998, 37:4000-4025.
Qin, D. et al., *Adv. Mater.* 1996, 8:917-919.
Jackman, R.J. et al., *Anal. Chem.* 1998, 11:2280-2287.

* cited by examiner

*Primary Examiner*—David M. Naff
(74) *Attorney, Agent, or Firm*—Wolf, Greenfield & Sacks, P.C.

(57) ABSTRACT

A method of patterning materials, such as proteins, on a contoured surface by depositing them onto protrusions on a surface, and a cell containment device that may be constructed by this method, are provided. The method may involve selectively depositing a material on a substrate including a contoured surface including protrusions and recesses. By applying a first fluid to the contoured surface and allowing the first fluid to distribute across only a portion of the contoured surface, a material may be deposited on the protrusions and not the recesses, or on the recesses and not the protrusions. Such a method may be used to selectively pattern cells or other materials on substrates.

27 Claims, 7 Drawing Sheets

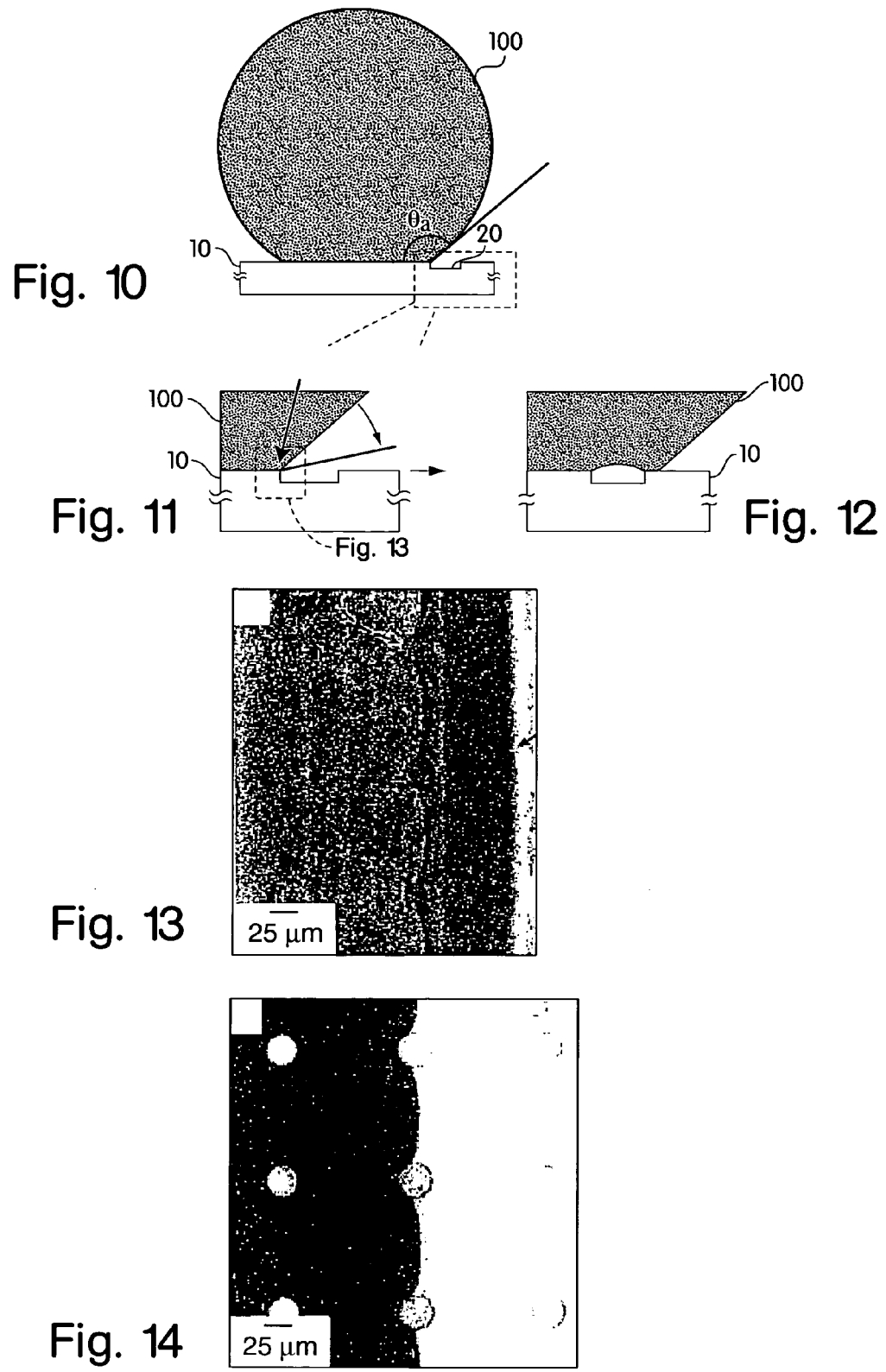

SELECTIVE DEPOSITION OF MATERIALS ON COUNTOURED SURFACES

RELATED APPLICATIONS

This application is a continuation of International Application No. PCT/US02/09149 filed Mar. 25, 2002, which was published under PCT Article 21(2) in English, and claims priority to U.S. provisional application Ser. No. 60/278,092, filed Mar. 23, 2001, each of which is incorporated by reference herein.

Funding for research leading to the invention(s) described and claimed herein was provided in part by Federal grants NSF ECS-9729405 and ONR N65236-97-1-5814. The government has certain rights in the invention.

BACKGROUND OF THE INVENTION

1. Field of the Invention

The present invention is directed to a method of patterning materials, such as proteins, on a contoured surface by depositing them onto protrusions on the surface and to a cell containment device that may be constructed by this method.

2. Description of the Related Art

A number of methods in biochemistry require a technique for patterning single cells with a high degree of spatial selectivity. Many laboratories are trying to take advantage of the high sensitivity of living cells in sensing units for biosensor applications; in these systems, the cells must be located precisely on the circuitry of the device. In tissue engineering, it may be useful to pattern different kinds of cells on different areas of a substrate in order to build defined architecture into multifunctional tissues. Automated technologies for high-throughput screening require the placement of cells in well-ordered arrays that can be addressed individually. Basic studies of cellular function and metabolism will also benefit from the ability to control the microenvironment of patterned cells, and to perturb them individually. Assays aimed at identifying the phenotype of a cell in a population of heterogeneously transfected cells might be simplified if individual cells were localized; the production of a fluorescently labeled gene product could be detected at the location, rather than remaining unidentified in solution.

Although cell-based assays are commonly available, applications involving patterned single cells have been limited by technological problems: e.g., the selective delivery of small volumes of liquid to a well with a 50 µm diameter, the placement of cells on a defined grid, and the prevention of non-selective adhesion and cell migration. Improving the technology to generate regular arrays of cells would make it possible to develop: i) analytical systems based on single cells for the detection of toxic agents; ii) systems for high-throughput screening of combinatorial libraries and gene products; iii) research tools to study the effect of the adhesive environment on the behavior of a cell; iv) new methods for the study of cellular function and metabolism at the level of single cells and individually isolated groups of cells.

To pattern single mammalian cells onto a substrate, the best strategy is often to pattern adhesive extracellular matrix (ECM) proteins onto that substrate. Current methods for patterning ECM proteins use self-assembled monolayers (SAMs) of alkanethiolates on gold, or of alkyltrichlorosiloxanes on silicon. Previously, it has been shown that mammalian cells can adhere to flat or contoured gold surfaces patterned with SAMs. Earlier work on patterning cells focused on their interaction with SAMs of alkylsiloxanes. Photolithographic patterning of siloxanes allowed the definition of patterns of functional groups that were recognized nonspecifically by various types of cells; complex biological ligands, however, are not compatible with these photolithographic methods. Microcontact printing has also been used to directly print patterns of proteins onto surfaces. (See U.S. Pat. Nos. 5,776,748 and 5,976,826, which are hereby incorporated by reference in their entirety.)

You et al. coated arrays of large wells (1-mm diameter) non-selectively with ECM proteins; mink lung cells were forced into the wells from a suspension by dragging a flat piece of PDMS across the array of wells. (You, A. J.; Jackman, R. J.; Whitesides, G. M.; Schreiber, S. L. *Chem. & Biol.* 1997, 4, 969-975.) Parce et al. used gravitational sedimentation to deposit cells in arrays of 50 µm wells that were fabricated using silicon micromachining. (Parce, J. W.; Owicki, J. C.; Kercso, K. M.; Sigal, G. B.; Wada, H. G.; Muir, V. C.; Bousse, L. J.; Ross, K. L.; Sikic, B. I.; McConnell, H. M. *Science* 1989, 246, 243-247.) Methods have also been developed for patterning cells onto surfaces using elastomeric membranes as resists against the adsorption of proteins and the adhesion of cells. (Ostuni, E; Kane, R.; Chen, C. S.; Ingber, D. E.; Whitesides, G. M. *Langmuir,* 2000, 16, 7811-7819.)

SUMMARY OF THE INVENTION

In one embodiment, the present invention is directed to a method of selectively depositing a material on a substrate including a contoured surface including a protrusion and a recess. The method includes applying a first fluid to the contoured surface of the substrate and allowing the first fluid to distribute across a portion of the contoured surface such that the first fluid contacts the protrusion and not the recess. The method also includes allowing a first material to deposit on the substrate where the substrate is in contact with the first fluid. Optionally, this method may further include applying a second fluid to the contoured surface of the substrate, allowing the second fluid to distribute across a portion of the contoured surface such that the second fluid contacts the recess, and allowing a second material to deposit on the substrate where the substrate is in contact with the second fluid. Optionally, the method may still further include applying a third fluid to the contoured surface of the substrate, allowing the third fluid to distribute across a portion of the contoured surface, and allowing a third material with an affinity for one of the first material and the second material to deposit on the substrate only where the one of the first material and the second material is deposited. In one embodiment of this method the first material is a cytophobic material, the second material is a cytophilic material and the third material is a cell.

In another embodiment, the present invention is directed to a method including selectively depositing a protein on an outward-facing portion of a protrusion of a contoured surface including a protrusion and a recess, at least one of the protrusion and recess having a maximum lateral dimension of no more than about 1 mm, while leaving the recess free of the protein.

In another embodiment, the present invention is directed to method of selectively depositing a material on a substrate having a contoured surface including a protrusion and a recess. The method includes applying a fluid to the contoured surface without urging the fluid against the surface mechanically, and allowing the fluid to contact the protrusion and not the recess. The method further includes allowing a first material to be deposited from the fluid onto the protrusion but not the recess.

In another embodiment, the present invention is directed to a cell containment device including a substrate including a contoured surface including a protrusion and a recess. The cell containment device further includes a cytophobic material connected to the protrusion and a cytophilic material connected to the recess.

In another embodiment, the present invention is directed to an article including a contoured surface including at least one protrusion and at least one recess, and a cytophilic agent on the surface within the recess. In this embodiment, the surface at the protrusion being free of the cytophilic agent.

In another embodiment, the present invention is directed to an article including a contoured surface including a plurality of protrusions and recesses, and at least one cell in at least one recess, wherein the at least one recess has a maximum lateral dimension of 500 μm.

In another embodiment, the present invention is directed to an article including a contoured surface including a plurality of protrusions and recesses, and a single cell in at least one recess.

BRIEF DESCRIPTION OF THE DRAWINGS

Preferred, non-limiting embodiments of the present invention will be described by way of example with reference to the accompanying drawings, in which:

FIG. 10 is a schematic of another embodiment of a substrate according to the present invention;

FIG. 11 is an expanded view of a portion of the embodiment of FIG. 10;

FIG. 12 is another expanded view of a portion of the embodiment of FIG. 10;

FIG. 13 is photocopy of an image from a microscope of a substrate according to another aspect of the present invention;

FIG. 14 is photocopy of an image from a microscope of a substrate according to another aspect of the present invention;

DETAILED DESCRIPTION OF THE INVENTION

Figure 1:
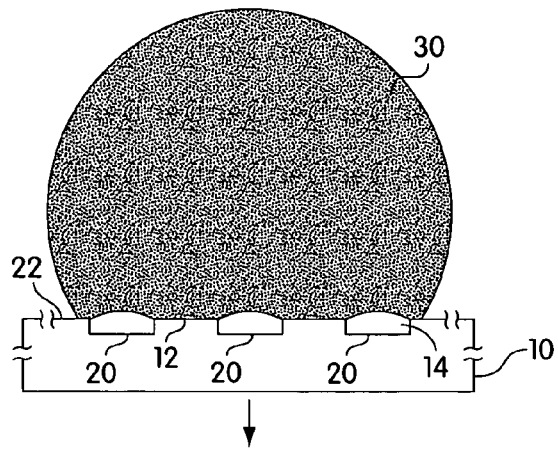
FIGS. 1-5 are a schematic of one embodiment of a substrate according to the present invention at different stages of one embodiment of the method of present invention.

In one embodiment, the present invention is directed to a method of selectively depositing a material on a substrate including a contoured surface including a protrusion and a recess. As used herein, a substrate is any material having a surface capable of having a contoured surface including a protrusion and a recess formed therein. Also as used herein, a protrusion may include a microprotrusion (a protrusion having a height and diameter of less than 1 mm), ridge, mesa, projection, or the like and a recess may include a microwell (a well having a depth and diameter of less than 1 mm), cavity, divot, hole, nook, or the like. Each of the protrusions and/or recesses may be of essentially any shape and size, as will be discussed below. A protrusion may also be defined by surrounding recesses, such as the area between microwells, and a recess may also be defined by surrounding protrusions, such as the area between microprotrusions.

The method includes applying a first fluid to the contoured surface of the substrate and allowing the first fluid to distribute across a portion of the contoured surface such that the first fluid contacts the protrusion and not the recess. The method also includes allowing a first material to deposit on the substrate where the substrate is in contact with the first fluid. Fluid is used herein to describe both traditional solutions and other liquids that may deposit a material on a surface, such as suspensions or pre-polymers that polymerize where in contact with the substrate. Deposit is used herein to broadly indicate that a material is left on a surface when fluid is removed and may refer to physical deposition, such as sedimentation, chemical and electrochemical deposition, electroless plating, biological attachment, and the like.

Optionally, this method may further include applying a second fluid to the contoured surface of the substrate, allowing the second fluid to distribute across a portion of the contoured surface such that the second fluid contacts the recess, and allowing a second material to deposit on the substrate where the substrate is in contact with the second fluid. Optionally, the method may still further include applying a third fluid to the contoured surface of the substrate, allowing the third fluid to distribute across a portion of the contoured surface, and allowing a third material with an affinity for one of the first material and the second material to deposit on the substrate only where the one of the first material and the second material is deposited. In one embodiment of this method the first material is a cytophobic material, the second material is a cytophilic material and the third material is a cell. As used herein, a cytophobic material is one which has no affinity for, or is repellant or toxic to, cells and a cytophilic material is one which has an affinity for cells. In some embodiments cells may be deposited in recesses. In these embodiments, it may be preferred to deposit a single cell within a recess, meaning that the recess is devoid of other cells.

In another embodiment, the present invention is directed to a cell containment device, including a substrate having a contoured surface including a protrusion and a recess, a cytophobic material connected to the protrusion and a cytophilic material connected to the recess.

The present invention exploits the observation that certain fluids do not enter recesses in a substrate when the fluid is applied to the substrate. This phenomenon is used to selectively deposit a material on a substrate. As the surface of the recess may then remain free for deposit of a second material, in some embodiments a fluid that does enter the recesses is applied to the substrate, allowing a second material to be deposited within the recesses. One example embodiment of a structure that may be made according to the present invention is a cell containment device including a cytophobic material deposited on the surface of a substrate and a cytophilic material deposited in recesses. Such a containment device may allow, for example, the study of individual cells and improved automation of certain processes involving cells.

The phenomenon by which certain liquids trap air in recesses on a surface can be explained using the Laplace-Young equation to define an advancing angle ($\theta_a$) (eq. 1);

$$\cos\theta_a = \frac{\gamma_{sv} - \gamma_{sl}}{\gamma_{lv}} \quad (1)$$

$\gamma$ is the interfacial tension of the solid-vapor (sv), solid-liquid (sl), and liquid-vapor (lv) interfaces. The solid-vapor interface of some materials, such as polydimethylsiloxane (PDMS), for example, has lower energy ($\gamma_{sv}$~21 dyn/cm) than the liquid-vapor interface of drops of some liquids, such as water, ($\gamma_{Lv}$ of water~73 dyn/cm). Fluids having values of $\theta_a>90°$ imply that the values of $\gamma_{sl}$ are high. Under such conditions, it is thermodynamically favorable for the area of all interfaces with the liquid to be minimized. Hence, a drop of liquid that contacts the flat regions of a substrate, but does not fill recesses, forms a system of lower free energy than one in which liquid contacts the entire surface of the substrate, including the recesses.

Cassie, A. B. D.; Baxter, S. *Trans. Faraday Soc.* 1944, 40, 546-551., which is hereby incorporated by reference in its entirety, discloses an equation (eq. 2) to describe the contact angle of a liquid on a contoured surface by taking into account the areas of the solid-liquid and liquid-vapor interfaces.

$$\cos\theta_b = f_1 \cos\theta_a - f_2 \quad (2)$$

In eq. 2, $\theta_b$ is the apparent contact angle, $\theta_a$ is the contact angle measured on the flat surface, $f_1$ is the area of the solid-liquid interface, and $f_2$ is the area of the liquid-vapor interface. Porosity causes the surface of a material on which a liquid has $\theta_a>90°$ (<90°) to appear more hydrophobic (hydrophilic) than a flat surface of the same material. Cassie and Shuttleworth used equation 2 to predict that a droplet of liquid with $\theta_a>90°$ would trap air inside recesses in a surface. (Cassie, A. B. D.; Baxter, S. *Trans. Faraday Soc.* 1944, 40, 546-551 and Shuttleworth, R.; Bailey, G. L. J. *Discuss. Faraday Soc.* 1948, 3, 16-22, which is hereby incorporated by reference in its entirety.) This prediction has been confirmed experimentally. The derivations assume that the contribution of gravitational force to the wetting behavior is minor; this assumption appears valid since the measured values of contact angles on porous surfaces are in agreement with the predicted ones.

Referring now to the figures, and in particular to FIGS. 10-12, a drop of fluid, namely liquid 100, with a high value of $\theta_a$ pins at the edge of a recess 20 until its contact angle on the wall of recess 20 reaches the advancing value. Liquids with a value of $\theta_a>90°$ reach the other edge of recess 20 before the angle between the liquid and the vertical wall reaches $\theta_a$; the edge of the liquid, therefore, advances over the face of recess 20 and traps air inside recess 20. Liquids with values of the receding contact angle ($\theta_r$)<90° fill recesses as drops of the liquids recede on the substrate. Accordingly, the portions of the method described herein where the liquid is not desired to enter the recess are preferably used with liquids that advance on the substrate ($\theta_a>90°$).

Referring now to FIGS. 1-5 and 21-24, one example embodiment of the method of the present invention will be described. The method includes providing a substrate 10 including recesses 20 and protrusions 22 on a contoured surface 12. Substrate 10 may be constructed in any manner and of any material(s) that allow a recess 20 or protrusion 22 to be formed therein. As recess 20 or protrusion 22 may be less than 100 µm across, substrate 10 may be constructed of a material that is able to be shaped to include an appropriately sized recess 20 or protrusion 22. Furthermore, as the geometry of recess 20 or protrusion 22 may impact whether a first fluid 30 enters recess 20, the material of substrate 10 may be capable of being accurately constructed in a desired geometry. Surface 12 of substrate 10 need not be flat, nor have any other particular geometry, as long as it allows first fluid 30 to contact it without entering recess 20. Substrate 10 may include any number of recesses 20 or protrusions 22 arranged in any desired pattern upon surface 12 of substrate 10. For example, substrate 10 may include evenly spaced recesses 20 or protrusions 22 arranged in a grid. By way of illustration, FIGS. 1-5 correspond to FIGS. 21-24, except that in FIGS. 1-5 recesses 20 are microwells and protrusion 22 is the space therebetween, while in FIGS. 21-24 protrusions 22 are microprotrusions and recesses 20 are the spaces therebetween.

Substrate 10 may have a surface that interacts with first fluid 30 such that fluid 30 does not enter recesses 20. For example, substrate 10 may be constructed out of a material upon which first fluid 30 has an advancing angle of about 90 degrees or greater. Substrate 10 may also have a surface that favors deposition of materials, such as a first material 32 from first fluid 30 or a second material 42 from a second fluid 40. Substrate 10 may also be constructed of a durable, relatively inexpensive material that is easy to construct and work with. For example, substrate 10 may be constructed of a material that may be easily cast or molded, such as many polymeric materials. As an alternate example, substrate 10 may be constructed of a material that is easily constructed with etching, photolithography or machining, such as a silicon-based material or a metal. A preferred polymeric substance for the construction of substrate 10 is an elastomer such as polydimethylsiloxane (PDMS), which is an easily molded, inexpensive, durable, transparent and relatively inert elastomer. PDMS is also hydrophobic, making it easier to bind proteins. The elastomeric nature of PDMS allows it to be stretched or deformed, and fitted to non-planar surfaces. PDMS is also permeable to O and $CO_2$. Other suitable elastomers are described in U.S. Pat. No. 5,512,131 and PCT publication nos. WO 96/29629 and WO 99/54786, which are hereby incorporated by reference in their entirety.

Substrate 10 constructed from PDMS or other moldable materials may be fabricated from reusable masters by replica molding. Where substrate 10 is constructed by replica molding, the size and shape of recess 20 may be defined using standard photolithography, e-beam writing or rapid prototyping as described in Xia, Y.; Whitesides, G. M. *Angew. Chem. Int. Ed. Engl.* 1998, 37, 4000-4025 and Qin, D.; Xia, Y.; Whitesides, G. M. *Adv. Mater.* 1996, 8, 917-919, which are hereby incorporated by reference in their entirety. Rapid prototyping is preferred for microwells greater than about 30 µm in diameter and standard photolithography is preferred for microwells between about 1-30 µm in diameter.

Recess 20 or protrusion 22 may be constructed in any manner that allows recess 20 to inhibit entry of particular fluids, such as first fluid 30. In some embodiments, recess 20 or protrusion 22 may also be constructed to promote entry of other fluids, such as a second fluid 40. For example, recess 20 or protrusion 22 may be symmetrical or irregular, and may have any shape or dimension that allows recess 20 to selectively inhibit the entry of particular fluids. The walls of recess 20 or protrusion 22 may be sloped inwardly or outwardly, or may be straight. By way of illustration, rather than limitation, recess 20 is assumed herein to be cylindrical and protrusion 22 is assumed to be defined by the area surrounding recess 20. Recess 20 may also have any dimensions that allow it to inhibit entry of particular fluids, such as first fluid 30, and, in some embodiments, to promote entry of other fluids, such as a second fluid 40. The dimensions of recess 20 may also be selected based upon a material to be contained within recess 20. For example, where recess 20 is to be constructed to contain cells, it may be sized to contain, for example, a single cell. Typically, recess 20 is less than about 100 µm in diameter and 50 µm in depth, however, it should be appreciated that these dimensions are dependent, for example, upon the material of substrate 10, the fluids used and the application.

The embodiment of the method illustrated in FIGS. 1-5 and 21-24 also includes applying first fluid 30 containing first material 32 to surface 12 of substrate 10, such that a bubble 14 is formed in recess 20 and substantially none of first fluid 30 enters recess 20. FIG. 1 illustrates substrate 10 with a drop of first fluid 30 thereon. First fluid 30 may be delivered to surface 12 by any conventional manner of transferring fluid, such as with a pipette or micropipette. In some instances, and particularly where the advancing angle between first fluid 30 and substrate 10 is about 90 degrees, it may be desired to apply first fluid 30 to substrate 10 in a controlled manner and to protect substrate 10 from shock, vibration, and the like while first fluid 30 is in contact with substrate 10 so that bubble 14 is not mechanically dislodged from recess 20.

First material 32 may be any material(s) desired to be deposited onto substrate 10. For example, first material 32 may be a material that may impart a desired surface activity to substrate 10. Accordingly, first material 32 may be any of a variety of materials, such as proteins, polymers, other chemicals or combinations thereof. By way of illustration, where substrate 10 is to become part of a cell containment device, first material 32 may be a cytophobic material intended to prevent cells from attaching to substrate 10 except at recesses 20. Cell-adhesion inhibiting agents are well known. Examples of cell-adhesion inhibiting agents include polyethylene glycol-based agents and bovine serum albumin (BSA). Those of ordinary skill in the art can easily screen agents for cell-adhesion promotion or inhibition as follows. Various agents can be applied to surfaces, cells can be applied to those surfaces, and the ability of the cells to adhere to the surface can be studied via morphology or other characteristics. This is routine for those of ordinary skill in the art.

The embodiment of the method illustrated in FIGS. 1-5 further includes allowing first material 32 to deposit on substrate 10 where substrate 10 is in contact with first fluid 30. How the deposit of first material 32 is accomplished may vary, for example, with the material of substrate 10 and the nature of first material 32 and first fluid 30. For example, the amount of time required for a desired amount of first material 32 to deposit may vary with these and other factors. By way of illustration, it has been found that 1 mg/ml BSA in PBS deposits satisfactorily on PDMS in approximately one hour at room temperature.

Other types of selective deposition of the materials may be accomplished in accordance with the principles of the invention in other manners. For example, metal deposition, such as "wet" electrochemical deposition or electroless deposition, can be carried out from fluid precursors defining electrochemical or electroless plating baths. Alternatively, a prepolymeric fluid precursor can be used, such as a fluid containing species that can react to form a thermoset polymer on projection 22, or a fluid pre-polymer that can be polymerized on protrusion 22 via photolysis, convective or radiative heat, free-radical polymerization, and the like. Additionally, a relatively low-melting polymer can be applied in a molten form and allowed to solidify on projection 22. These and other forms of polymerization are known to those of ordinary skill in the art and can be applied to the techniques of the present invention without undue experimentation. All types of polymerization, including cationic, anionic, copolymerization, chain copolymerization, cross-linking, and the like can be employed, and essentially any type of polymer or copolymer formable from a fluid precursor can be patterned in accordance with the invention. An example, non-limiting list of polymers that are suitable include polyurethane, polyamides, polyamines, polycarbonates, polyacetylenes and polydiacetylenes, polyphosphazenes, polysiloxanes, polyolefins, polyesters, polyethers, poly(ether ketones), poly(alkylene oxides), poly(ethylene terephthalate), poly(methyl methacrylate), polystyrene, and derivatives and block, random, radial, linear, or teleblock copolymers, cross-linkable materials such as proteinaceous material and/or blends of the above. Gels may be suitable. Also suitable are polymers formed from monomeric alkyl acrylates, alkyl methacrylates, alpha-methylstyrene, vinyl chloride and other halogen-containing monomers, maleic anhydride, acrylic acid, acrylonitrile, specifically, methyl methacrylate, imides, carbonates, hexafluoroisopropyl methacrylate, acrylonitrile, bromophenyl acrylates or bromophenyl methacrylates, and the like. Monomers can be used alone, or mixtures of different monomers can be used to form homopolymers and copolymers. Non-linear and ferroelectric polymers can be advantageous. The particular polymer, copolymer, blend, gel, protein or other material selected is not critical to the invention, and those of skill in the art can tailor a particular material for any of a wide variety of applications.

As yet another example, a variety of organic electroluminescent materials may also be used, including those described in the following articles, each incorporated herein by reference: Renak, et al., "Microlithographic Process for Patterning Conjugated Emissive Polymers", *Adv. Mater.*, 1997, 9, 5, 392-394; Yam, "Plastics Get Wired", *Scientific American*, July 1995, 83-87; Kijima, et al., "RGB Luminescence from Passive-Matrix Organic LED's", *IEEE Transactions on Electron Devices*, 44, 8, August 1997; Shen, et al., "Three-Color, Tunable, Organic Light-Emitting Devices", *Science*, 6, Jun. 27, 1997; Burrows, et al., "Achieving Full-Color Organic Light-Emitting Devices for Lightweight Flat-Panel Displays", *IEEE Transactions on Electron Devices*, 44, 8, August 1992.

By way of another example, according to one embodiment, a polymerizable or cross-linkable species (optionally in a fluid carrier) including an admixed biochemically active agent such as a protein can be made to form a pattern on a substrate surface according to the described technique. For example, carboxylated Dextran™ can carry admixed protein, be applied to surface 12 of substrate 10, and hardened. Where the Dextran™ carries admixed biologically active agent, the substrate can be exposed to a medium suspected of containing a biological binding partner of the biochemical agent, and any biochemical binding or other interaction detected via, for example, diffraction.

In some embodiments, first material 32 may be combined with a compatible carrier to form first fluid 30. The carrier may be selected such that first fluid 30 has an advancing angle of more than about 90 degrees with substrate 10 and promotes, or does not inhibit, the deposit of first material 32 on substrate 10. An acceptable carrier for many biological materials, such as proteins, is phosphate buffered saline (PBS).

Figure 2:
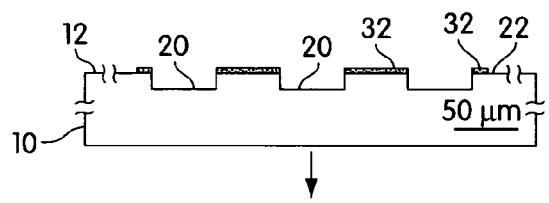

As illustrated in FIG. 2, first fluid 30 may be removed from substrate 10, leaving first material 32 deposited thereon. Where first fluid 30 it to be removed from substrate 10, it may be removed in any manner that will remove first fluid 30 without removing first material 32 deposited on substrate 10. For example, first fluid 30 may be removed from substrate 10 by vacuum, absorption, drying, and the like.

Figure 3:
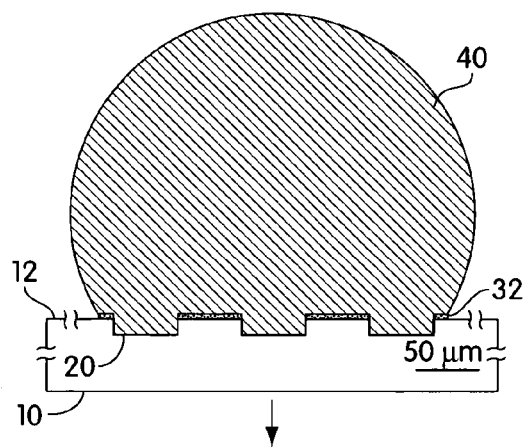

As illustrated in FIG. 3, in some embodiments of the invention, the method may further include applying second fluid 40 containing second material 42 to surface 12 of substrate 10, such that second fluid 40 enters recess 20. Second fluid 40 may be delivered to surface 12 by any conventional manner of transferring fluid, such as with a pipette or micropipette. In some instances, and particularly where the contact angle between second fluid 40 and substrate 10 is about 90 degrees, it may be desired to apply shock, vibration, and the like to, substrate 10 while second fluid 40 is in contact with substrate 10 so that any bubble 14 is mechanically dislodged from recess 20. Alternatively, a vacuum may be applied to the environment of second fluid 40 and substrate 10 to promote the release of any bubble 14. For example, a vacuum of about 400 mm Hg was found to loosen bubbles in some applications.

Second material 42 may be any material(s) desired to be deposited within recesses 20. In some embodiments, second material 42 is preferred not to deposit where first material 32 has deposited. Second material 42 may be a material that may impart a desired surface activity to substrate 10. Accordingly, second material 42 may be a variety of materials, such as proteins, polymers, other chemicals or combinations thereof. By way of illustration, where substrate 10 is to become part of a cell containment device, second material 42 may be a cytophilic material intended to promote the attachment of cells to substrate 10 within recess 20.

In one embodiment, second material 42 can be a cell-adhesion promoter, i.e. second material 42 can have physical (e.g., "sticky" materials) and/or chemical properties that allow cell adherence to second material 42 while maintaining the integrity of the cell. Cell adhesion can be achieved by specific or non-specific interactions. Surfaces which promote non-specific interactions of proteins adhere most cells. Examples of such surfaces include ionic or charged surfaces. Hydrophilic surfaces also promote non-specific protein absorption and cell adhesion. An example of a surface involved in non-specific interactions includes polymer surfaces used in biomaterials such as polylysine or plasma-treated polystyrene. Cell-specific interactions generally result when a cell has a receptor which recognizes certain surfaces. For example, mammalian cells have receptors which recognize extracellular matrix proteins. Examples of cell-adhesion promoting agents include extracellular matrix proteins such as vitronectin, laminin, fibronectin (FN), collagens and gelatins. Alternatively, a surface can be modified with antibodies which recognize certain cellular receptors.

Many of the fluids and materials described for first fluid 30 and first material 32 may also find use as second fluid 40 and second material 42 if their surface interaction with the substrate is modified, or a vacuum or other technique used to remove bubbles 14 from substrate 10.

Second material 42 may be combined with a compatible carrier to form second fluid 40. The carrier may be selected such that second fluid 40 has a contact angle of less than about 90 degrees with the substrate and promotes, or does inhibit, the deposit of second material 42 on substrate 10.

The embodiment of the method illustrated in FIGS. 1-5 further includes allowing second material 42 to deposit on substrate 10 where substrate 10 is in contact with second fluid 40. How the deposit of second material 42 is accomplished may vary, for example, with the material of substrate 10 and the nature of second material 42 and second fluid 40. For example, the amount of time required for a desired amount of second material 42 to deposit may vary with these and other factors. For example, it has been found that 50 μg/ml FN in PBS deposits satisfactorily on PDMS in approximately one hour at room temperature.

Figure 4:
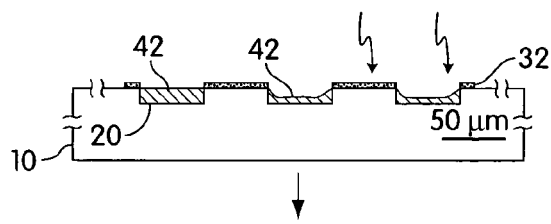
Figure 5:
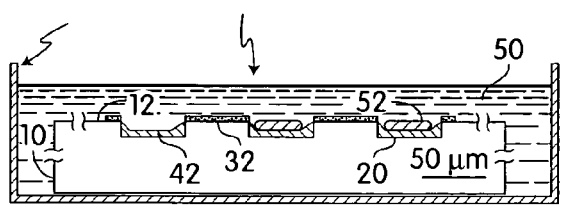

As illustrated in FIG. 4, second fluid 40 may be removed from substrate 10, leaving second material 42 deposited thereon. Where second fluid 40 is to be removed from substrate 10, it may be removed in any manner that will remove second fluid 40 without removing second material 42 deposited on substrate 10. For example, second fluid 40 may be removed from substrate 10 by vacuum, absorption, drying, and the like.

As illustrated in FIG, 5, the method may still further include applying a third fluid 50 containing a third material 52 with an affinity for one of first material 32 and second material 42 to upper surface 12 of substrate 10 and allowing third material 52 to deposit on substrate 10 where the one of the first material 32 and second material 42 is deposited. Third fluid 50 may be delivered to surface 12 by any conventional manner of transferring fluid, such as with a pipette or micropipette. Alternatively, substrate 10 may be immersed in third fluid 50 such that third fluid 50 contacts surface 12. In some instances, and particularly where the contact angle between third fluid 50 and substrate 10 is about 90 degrees, it may be desired to apply shock, vibration, and the like to substrate 10 while third fluid 50 is in contact with substrate 10 so that any bubble 14 is mechanically dislodged from recess 20. Alternatively, a vacuum may be applied to the environment of third fluid 50 and substrate 10 to promote the release of any bubble 14.

Third material 52 may be any material(s) desired to be deposited within recesses 20. In some embodiments, third material 52 is preferred not to deposit where first material 32 has deposited. Third material 52 may be a material that is desired to be isolated, for example for study. Accordingly, third material 52 may be a variety of materials, such as proteins, polymers, other chemicals, cells or combinations thereof. By way of illustration, where substrate 10 is part of a cell containment device, third material 52 may be a cell of interest. Any cell of interest to those skilled in the art may be patterned this way. An example of a cell that may be contained within a recess 20 is a bovine adrenal capillary endothelial (BCE) cell.

Third material 52 may be combined with any compatible carrier to form third fluid 50. The carrier may be selected such that third fluid 50 has a contact angle of less than about 90 degrees with the substrate and promotes, or does not inhibit, the deposit of third material 52 on substrate 10.

The embodiment of the method illustrated in FIGS. 1-5 further includes allowing third material 52 to deposit on substrate 10 where second material 42 is deposited. How the deposit of third material 52 is accomplished may vary, for example, with the material of substrate 10 and the nature of third material 52 and third fluid 40. For example, the amount of time required for a desired amount of third material 52 to deposit may vary with these and other factors. Where third material 52 includes living cells, the deposition process may include incubation. For example, it has been found that BCE cells in a chemically defined medium (10 µg/mL high density lipoprotein, 5 µg/mL transferrin, 5 ng/mL bFGF in BSA/DMEM), incubated in 10% $CO_2$ at 37° C. for 4 hours in recesses 20 deposited satisfactorily.

EXAMPLES

Example 1

An experiment was performed to demonstrate the feasibility of production of substrates including arrays of microwells. PDMS substrates were prepared as described in Jackman, R. J.; Duffy, D. C.; Ostuni, E.; Willmore, N. D.; Whitesides, G. M. *Anal. Chem.* 1998, 11, 2280-2287, which is incorporated herein by reference in its entirety. To summarize, a master consisting of posts of photoresist supported on a silicon wafer was prepared photolithographically; the height of the posts, which corresponds to the depth of the microwells, was controlled by the choice of the photoresist and the spinning rate. The chrome masks used for photolithography had circular features with diameters between 25 µm and 50 µm and spacing between 50 µm and 75 µm; masks were prepared by Advanced Reproductions, North Andover, Mass. The PDMS (Dow Corning, Sylgard 184) was cured against these masters at 60° C. for two hours and peeled away from the silicon wafers to give an array of microwells molded into the surface of the polymer. Substrates were then cut to the desired size (typically 1-2 cm²) and washed with ethanol and distilled water before use. These experiments demonstrate that production of substrates having arrays of microwells is feasible and relatively straightforward.

Example 2

Experiments were performed to demonstrate that fluids having an advancing angle of greater than 90 degrees do not enter microwells and fluids having advancing angles of less that 90 degrees do enter microwells. First, the contact angles of various fluids on PDMS were measured using a contact angle goniometer (Rame-Hart, Mountain Lakes, N.J.). Advancing contact angles were measured for three separate drops on each substrate by delivering/withdrawing aliquots (3×5 µl) of fluid with a micropipette (Matrix Technologies, MicroElectrapette). The results are reported in Table I. Each entry in Table I is the average of the three measurements. Occasionally, the drops pinned on heterogeneities on the surface of the polymer; in such cases, the values of the contact angles deviated from the average by more than 50% and new measurements were taken on another region of the surface.

Next, the fluids for which the advancing angle was known were applied to a substrate including an array of microwells to determine if the fluid entered the microwells. The results of this experiment are reported in Table I.

TABLE I

Advancing contact angles of various fluids on flat PDMS substrates. The columns under "filling" report whether the tested liquids filled wells with the specified dimensions (reported in the format "diameter(depth)," both in micrometers). A "+" indicates wells that are filled by the liquid and a "−" indicates cases when filling was not observed.

|  | $\theta_{a(PDMS)}$ | Filling | | |
| --- | --- | --- | --- | --- |
|  | (±5 deg) | 25(5) | 50(1.3) | 50(5) |
| Distilled Water | 111 | − | − | − |
| Fibronectin/PBS (50 µg/mL) | 109 | − | − | − |
| BSA/PBS (1 mg/mL) | 100 | − | − | − |
| Ethylene glycol (EG) | 92[a] | +/−[b] | +/−[b] | +/−[b] |
| Tri(ethylene glycol) | 76[a] | + | + | + |
| Butan-1-ol | 36[a] | + | + | + |
| Ethanol | 31[a] | + | + | + |

[a]Obtained from You, A. J.; Jackman, R. J.; Whitesides, G. M.; Schreiber, S. L. Chem. & Biol. 1997, 4, 969-975.
[b]EG does not fill the wells immediately; over minutes, the trapped bubbles escape.

Figure 6:
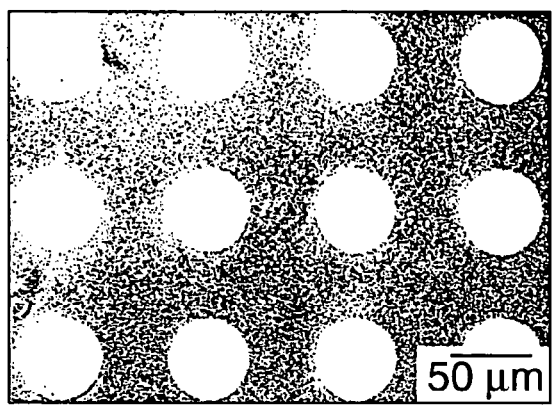
FIG. 6 is photocopy of an image from a microscope of a substrate according to another aspect of the present invention.

When drops of aqueous fluids with values of $\theta_a > 90°$ were placed on top of a substrate that presented microwells and allowed to spread, air was trapped in the microwells. FIG. 6 shows the appearance of an array of microwells covered with a drop of solution of BSA (1 mg/mL) in PBS buffer ($\theta_a = 100°$). Microwells filled with air were much brighter than the rest of the substrate when imaging the system in reflection mode on an inverted microscope (light coming from the "bottom" of the sample) using light of high intensity (100 W Hg arc lamp). The difference between the index of refraction of PDMS and air (ca. 0.4) is higher than the difference between PDMS and buffer (ca. 0.05); hence, the microwells that were filled with air reflected more light and appeared brighter than the rest of the sample.

Figure 7:
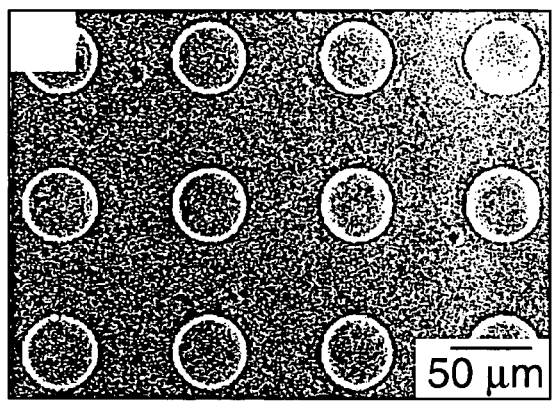
FIG. 7 is photocopy of an image from a microscope of a substrate according to another aspect of the present invention.

Liquids with values of $\theta_a > 90°$ were allowed to cover the entire surface of the substrates by detaching the air from the microwells with a brief exposure of the system to house vacuum for 30 sec; the bubbles in the microwells expanded and detached when vacuum was applied, and the microwells filled when vacuum was released. Microwells that were filled with liquid were not brighter than the rest of the surface, as illustrated in FIG. 7.

Figure 8:
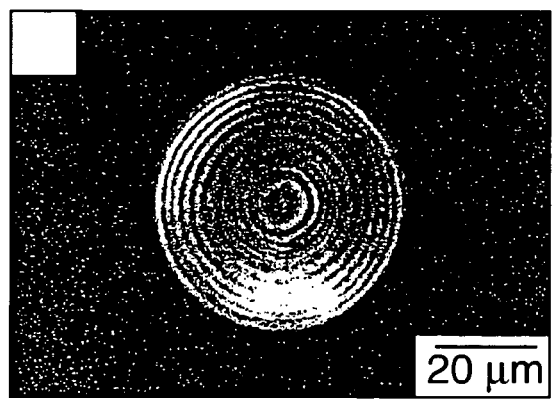
FIG. 8 is photocopy of an image from a microscope of a substrate according to another aspect of the present invention.
Figure 9:
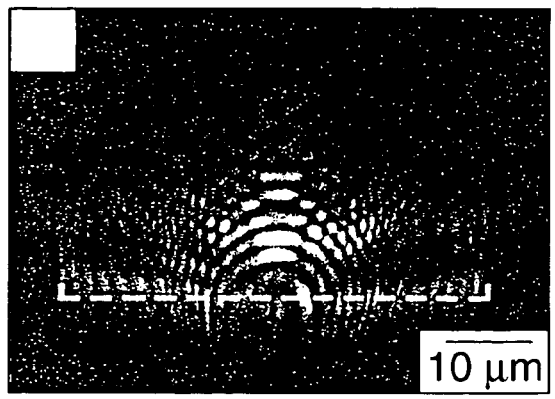
FIG. 9 is photocopy of an image from a microscope of a substrate according to another aspect of the present invention.

The results obtained with optical microscopy were confirmed using confocal microscopy. FIG. 8 shows a confocal image of a well filled with air; the image was obtained in reflection mode (light coming from the "top" of the sample). A complex optical diffraction pattern produced by the light reflected from the air-filled cavity was observed, as illustrated in FIG. 9. Indistinguishable observations were made with microwells 50 µm wide and 1.3 µm deep, 25 µm wide and 5 µm deep and 50 µm wide and 50 µm deep when distilled water or PBS buffer were used to cover the substrate. Air was also trapped in the wells when the substrates were placed upside-down, on top of a drop of liquid.

Liquids such as ethanol and butan-1-ol having values of $\theta_a < 90°$ on PDMS filled the microwells. When ethylene glycol (EG, $\theta_a = 92 \pm 5°$) covered the microwells, air was trapped in the wells, but the bubbles escaped within minutes.

These experiments demonstrate that fluids having an advancing angle of greater than about 90 degrees do not enter microwells, while those having an advancing angle of less than about 90 degrees do enter microwells.

Example 3

Figure 15:
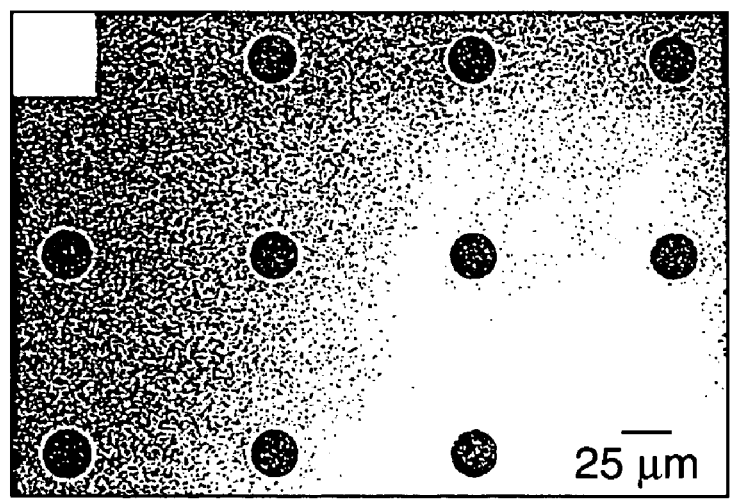
FIG. 15 is photocopy of an image from a microscope of a substrate according to another aspect of the present invention.

Experiments were performed to demonstrate that materials could be selectively deposited on a substrate including microwells. The surface between the microwells was first coated with BSA by placing a solution of the protein in PBS on the substrate for 1 hour at room temperature. In this interval, air trapped in the microwells protected their surfaces from contact with the solution of BSA (FIG. 6); the trapped air effectively acted as a resist against the adsorption of protein. This result was confirmed by performing the same incubation with a solution of fluorescently labeled BSA (FIG. 15).

Following the adsorption of BSA on the regions between the microwells, the substrate was rinsed with PBS and exposed to house vacuum for 30 seconds to remove the air bubbles from the microwells and ensure that liquid filled them. The PBS was then exchanged with a solution of FN (50 µg/mL) in buffer. FN adsorbed on those hydrophobic regions of the surface not already covered with BSA, that is the surface of the microwells; the adsorbed BSA protected the regions between the microwells from the adsorption of FN.

Figure 16:
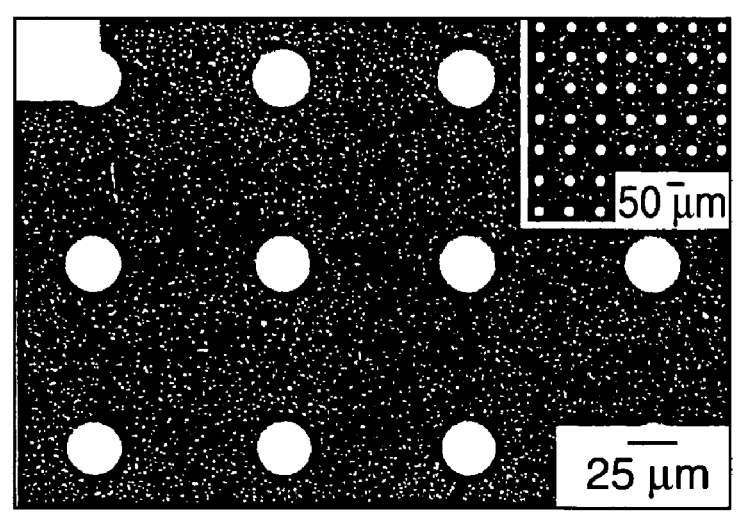
FIG. 16 is photocopy of an image from a microscope of a substrate according to another aspect of the present invention.
Figure 17:
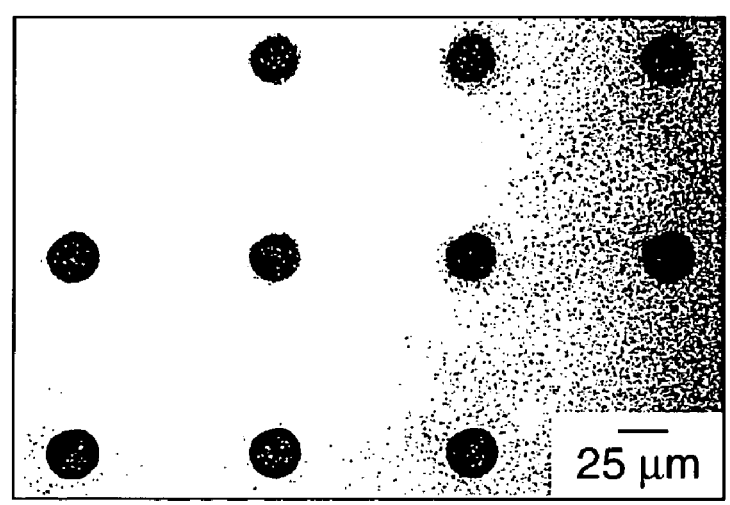
FIG. 17 is photocopy of an image from a microscope of a substrate according to another aspect of the present invention.

Immunofluorescence staining of FN confirmed that this protein was delivered and adsorbed to the microwells selectively (FIG. 16). A drop of FN left on top of an uncoated PDMS substrate, allowed the protein to adsorb only to the regions of the array between the wells (FIG. 17).

Figure 25:
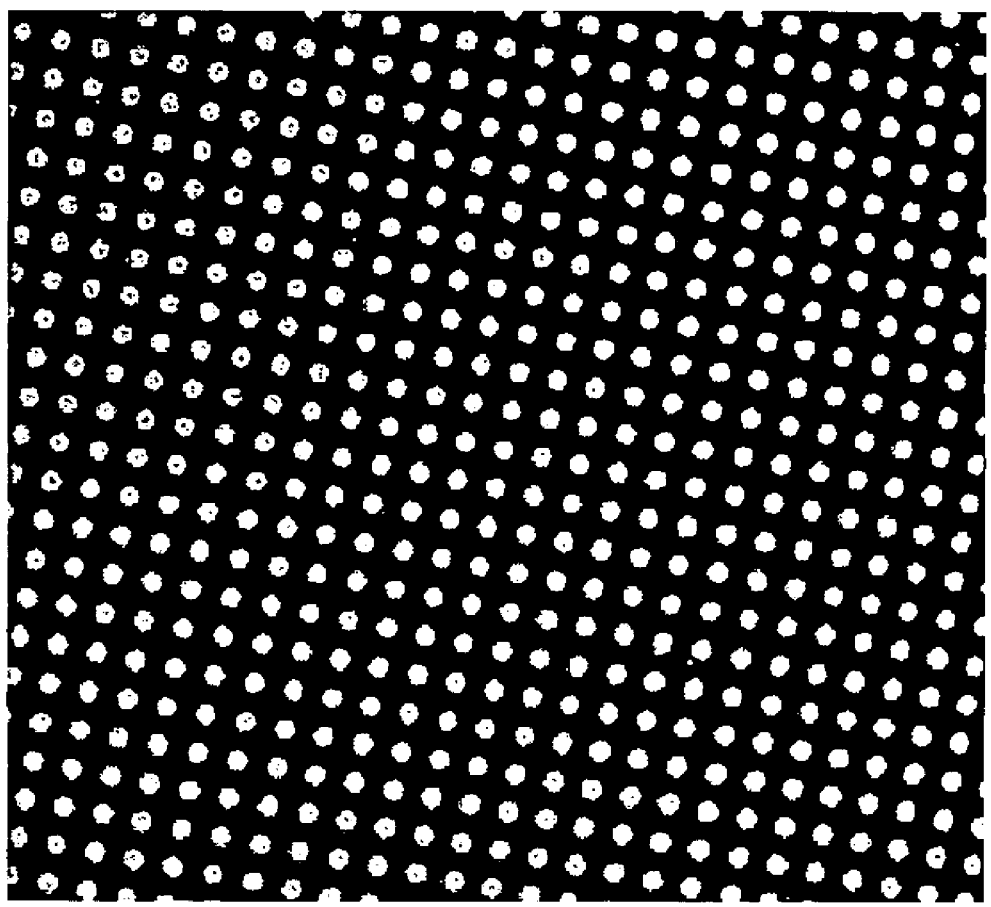
FIG. 25 is a photocopy of an image from a microscope of a substrate according to another aspect of the present invention.

These experiments demonstrate that it is possible to selectively deposit material on a substrate including microwells according to one embodiment of the method of the present invention. A similar experiment was performed on a substrate including a plurality of microprotrusions. Immunofluorescence staining of FN confirmed that this protein was delivered and adsorbed to the microprotrusions selectively (FIG. 25).

Example 4

An experiment was performed to demonstrate that the method of the present invention is capable of producing a working cell containment device. Initially, PDMS substrates were placed inside sterile Petri dishes. A drop of BSA (Intergen Company, Purchase, N.Y.; 1 mg/mL) in PBS buffer was placed on top of the substrate for 1 hour to allow the protein to deposit on the surface between wells. The liquid trapped air bubbles inside the microwells; these air bubbles protected the interior surface of the wells from contact with the solution containing BSA. Shaking or vibrating the substrate was avoided to prevent accidental dislodgment of the bubbles. The substrate was then washed gently with PBS three times. Brief exposure (30 sec) of the substrates to house vacuum (ca. 400 mm Hg) ensured that all the bubbles escaped from the microwells during the washing process.

The PBS wash was exchanged with a solution of FN (Collaborative Biomedical; 50 µg/mL) in PBS by rapidly aspirating the buffer and placing the solution of FN on the surface of the substrate; during this procedure, drying the sample was avoided to prevent the formation of bubbles and damage to the deposited BSA. The deposit of FN on the PDMS was then allowed to proceed at room temperature for 1 hr.

Bovine adrenal capillary endothelial (BCE) cells were cultured under 10% $CO_2$ on petri dishes (Falcon) coated with gelatin in Dulbecco's Modified Eagle's Medium (DMEM) containing 10% calf serum, 2 mM glutamine, 100 µg/mL streptomycin, 100 µg/mL penicillin, and 1 ng/mL basic fibroblast growth factor (bFGF). Prior to incubation with the polymeric substrate, cells were dissociated from culture plates with trypsin-EDTA and washed in DMEM containing 1% BSA (BSA/DMEM). The cells were placed on the substrates in chemically defined medium (10 µg/mL high density lipoprotein, 5 µg/mL transferrin, 5 ng/mL bFGF in BSA/DMEM) and incubated in 10% $CO_2$ at 37° C. In a typical experiment, the PDMS substrate, patterned with proteins as described above, was immersed in 4 mL of solution that contained $10^5$ cells. A typical incubation time was 4 hr, and cells were routinely cultured for up to 48 h in the microwells. Cells were also able to be patterned in serum-containing medium for 48 hours after being seeded in serum-free medium.

Figure 18:
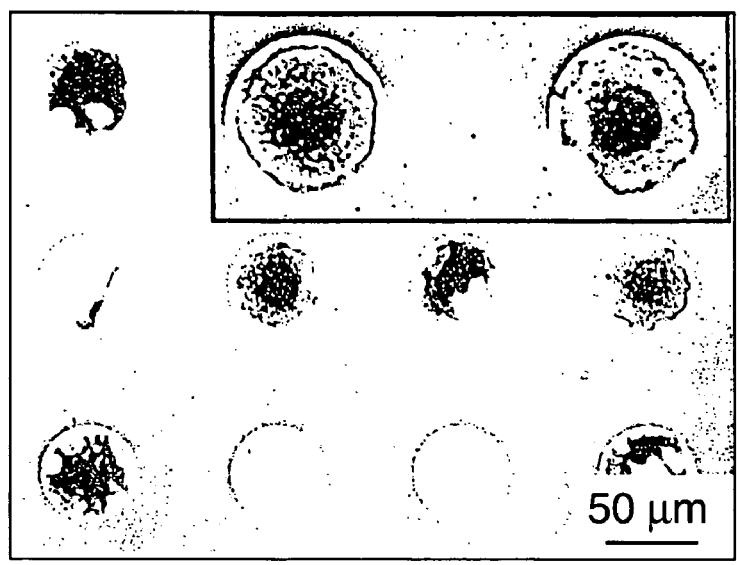
FIG. 18 is photocopy of an image from a microscope of a substrate according to another aspect of the present invention.
Figure 19:
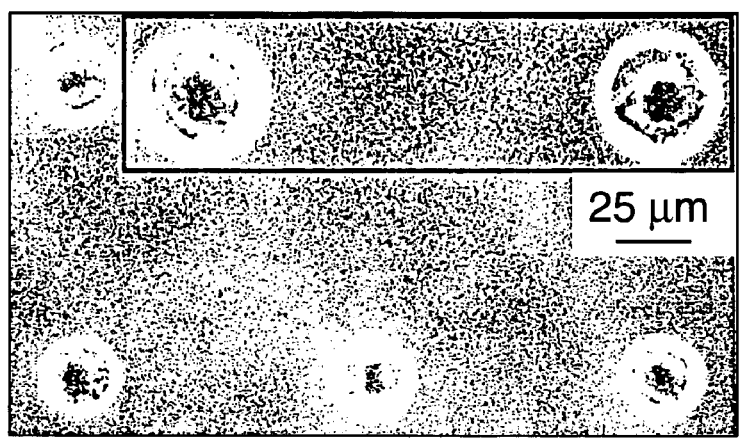
FIG. 19 is photocopy of an image from a microscope of a substrate according to another aspect of the present invention.
Figure 20:
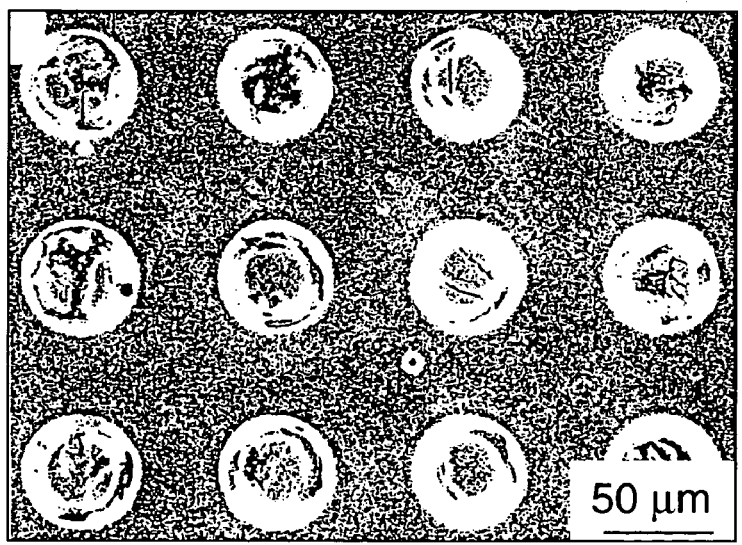
FIG. 20 is photocopy of an image from a microscope of a substrate according to another aspect of the present invention.
Figure 21:
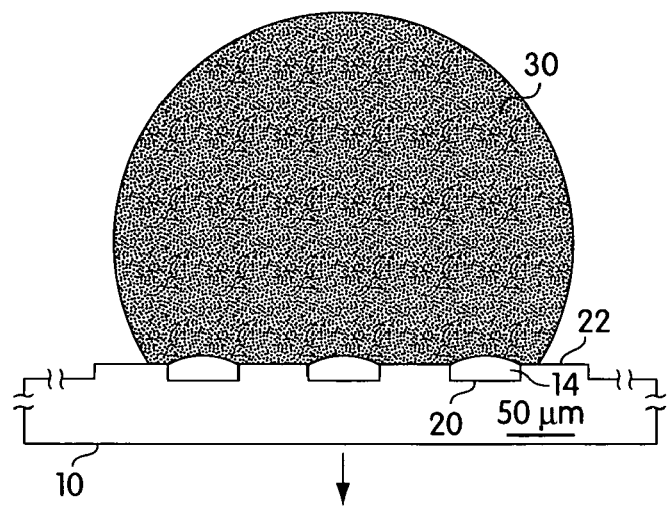
FIGS. 21-24 are a schematic of another embodiment of a substrate according to the present invention at different stages of another embodiment of the method of present invention.
Figure 22:
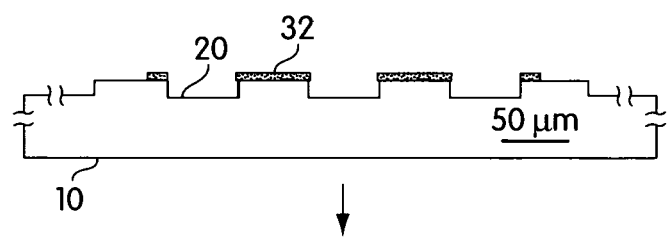
Figure 23:
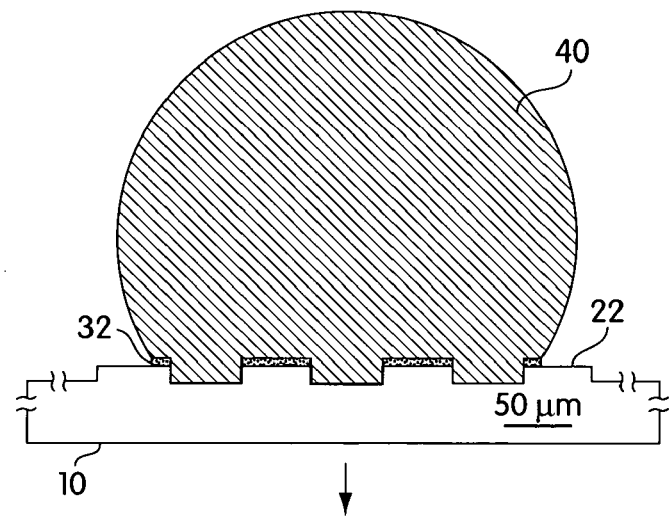
Figure 24:
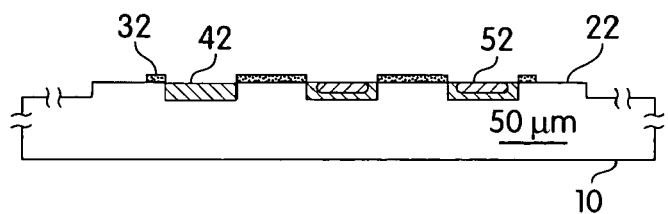

As expected, cells selectively adhered to the microwells (FIGS. 18-20). Cells attached in ca. 70% of microwells 50 µm in diameter and 1.3 µm deep (FIG. 18). The occupancy of cells 25 µm in diameter and 5 µm deep wells was lower (40%) (FIG. 19).

The cells in suspension reached the surface of the substrate by gravitational sedimentation; once on the surface, cells rolled under the influence of motion in the liquid. Cells generally adhered to the adhesive island of FN presented at the bottom of wells with depths between 1.3 and 5 µm. The depth of the wells prevented the cells from binding to the neighboring islands of FN, however, cells occasionally "bridged" two shallow (1.3 µm deep) microwells.

When using microwells that were 50 µm deep, the walls of the microwells presented an adhesive surface that supported the adhesion of whole cells rather than just parts of cells (FIG. 20); it was also possible to find multiple cells in the same 50 µm in diameter and 50 µm deep microwell. In such wells, a large fraction of cells adhered preferentially to the walls of the microwells. This is not surprising, because, in the case of the 50 µm in diameter and 50 µm deep microwells, the ratio of the area of the wall of the well to the area of the bottom of the well is 4; hence, cells adhere preferentially to the walls of the wells.

It will be understood that each of the elements described herein, or two or more together, may be modified or may also find utility in other applications differing from those described above. While particular embodiments of the invention have been illustrated and described, the present invention is not intended to be limited to the details shown, since various modifications and substitutions may be made without departing in any way from the spirit of the present invention as defined by the following claims.

The invention claimed is:

1. A method of selectively depositing a material on a substrate including a contoured surface including a protrusion and a recess, the method comprising:
    applying a first fluid to the contoured surface of the substrate;
    allowing the first fluid to distribute across a portion of the contoured surface such that the first fluid contacts the protrusion and not the recess; and allowing a first material to deposit from the first fluid on the protrusion of the substrate.

2. The method of claim 1, further comprising:
applying a second fluid to the contoured surface of the substrate;
allowing the second fluid to distribute across a portion of the contoured surface such that the second fluid contacts the recess; and
allowing a second material to deposit from the second fluid on the recess of the substrate.

3. The method of claim 2, further comprising:
applying a third fluid to the contoured surface of the substrate;
allowing the third fluid to distribute across a portion of the contoured surface; and
allowing a third material with an affinity for one of the first material and the second material to deposit from the third fluid on the substrate only where the one of the first material and the second material is deposited.

4. The method of claim 3, wherein the first material is a protein.

5. The method of claim 4, wherein the second material is a protein.

6. The method of claim 5, wherein the first material is cytophobic.

7. The method of claim 6, wherein the second material is cytophilic.

8. The method of claim 7, wherein the third material is a cell.

9. The method of claim 1, wherein the recess comprises a microwell.

10. The method of claim 9, wherein the microwell is less than 1 millimeter in width and depth.

11. The method of claim 10, wherein the microwell is less than 100 micrometers in width and depth.

12. The method of claim 11, wherein the microwell is less than 50 micrometers in width and depth.

13. The method of claim 1, wherein the protrusion comprises a microprotrusion.

14. The method of claim 13, wherein the microprotrusion is less than 1 millimeter in width and height.

15. The method of claim 14, wherein the microprotrusion is less than 100 micrometers in width and height.

16. The method of claim 15, wherein the microprotrusion is less than 50 micrometers in width and height.

17. The method of claim 1, wherein the substrate comprises a flexible material.

18. The method of claim 1, wherein the substrate comprises a polymer.

19. The method of claim 18, wherein the substrate comprises polydimethylsiloxane.

20. The method of claim 1, wherein the substrate comprises a plurality of recesses.

21. The method of claim 20, wherein the recess comprises a portion of the substrate between the protrusions.

22. The method of claim 1, wherein the substrate comprises a plurality of protrusions.

23. The method of claim 22, wherein the protrusion comprises a portion of the substrate between the recesses.

24. The method of claim 1, wherein the first fluid has an advancing angle of greater than about 90°.

25. The method of claim 3, wherein at least one of the second fluid and the third fluid has an advancing angle of less than about 90°.

26. A method, comprising:
selectively depositing a protein on an outward-facing portion of a protrusion of a contoured surface including a protrusion and a recess, at least one of the protrusion and recess having a maximum lateral dimension of no more than about 1 mm, while leaving the recess free of the protein.

27. A method of selectively depositing a material on a substrate having a contoured surface including a protrusion and a recess, the method comprising:
applying a fluid to the contoured surface without urging the fluid against the surface mechanically, and allowing the fluid to contact the protrusion and not the recess; and
allowing a first material to be deposited from the fluid onto the protrusion but not the recess.

* * * * *